United States Patent [19]

van Andel

[11] Patent Number: Plant 5,504

[45] Date of Patent: Jul. 2, 1985

[54] CARNATION NAMED STANDISC

[75] Inventor: Jacob van Andel, Aalsmeer, Netherlands

[73] Assignee: B. V. Handelskwekerij, M. C. van Staaveren, Aalsmeer, Netherlands

[21] Appl. No.: 556,262

[22] Filed: Nov. 30, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new carnation cultivar distinguished by its medium sized blooms of a generally pink and white coloration borne raceme on long, strong stems, the flower petals occasionally bearing longitudinal stripes of a dark red color which produce a very unusual variegated pink and white overall presentation.

1 Drawing Figure

BACKGROUND OF THE NEW PLANT

This new carnation cultivar was originated by me as a seedling hybrid at Aalsmeer, Holland, the seedling resulting from a cross of selected unpatented varieties grown in greenhouse at Aalsmeer for breeding purposes, my object being to produce a new flower color in a plant having better production and disease resistance. This plant was selected by me for propagation because of its light pink and white variegation in a small button-type flower and propagation of this new seedling was accomplished by means of cuttings with such favorable results that propagation was continued at Aalsmeer through several successive generations, which demonstrated clearly that the distinguishing characteristics of the new seedling would be retained from generation to generation so that they appeared to be firmly fixed.

DESCRIPTION OF THE DRAWING

My new carnation plant is illustrated by the accompanying full color photographic drawing which shows the inflorescence and buds in various stages as they appear on a number of flowering stems, the color reproduction being as true as can be reasonably obtained by conventional photographic procedures.

DESCRIPTION OF THE NEW PLANT

The following is a detailed description of my new carnation cultivar based upon observation of plants grown under conventional greenhouse procedures at Aalsmeer, Holland, the color designations being according to The R.H.S. Colour Chart published by The Royal Horticultural Society of London, England.

THE PLANT

Origin: Seedling.

Parentage:

*Seed parent.*—The variety "Stadivers" (unpatented).

*Pollen parent.*—The variety 07-2H (unpatented) identified in my breeding records by the stated number and maintained in my collection of carnation plants at Aalsmeer, Holland.

Classification:

*Botanic.*—*Dianthus caryophyllus.*

*Commercial.*—Spray carnation. p0 Form: Tall bush.

Growth: Upright with good strength and normal branching character.

Foliage:

*Quantity.*—Abundant.

*Number of leaves.*—Depending on season.

*Size of leaf.*—Medium.

*Shape.*—Oblong.

*Texture.*—Smooth.

*Color.*—Both upper side and under side — Blue/-Green with waxy layer.

THE BUD

Size: Medium.

*Diameter.*—About 15 mm.

*Length.*—About 30 mm.

Shape: Generally ovoid with pointed apex becoming cylindrical before sepals divide.

Sepals: Hooded over bud, stand up upon opening and curl back as the bloom expands.

*Color.*—Inside and outside —Grey/Green.

Calyx:

*Shape.*—Funnel-shaped.

*Size.*—Medium.

*Aspect.*—Smooth.

*Splitting.*—The calyx rarely splits.

THE FLOWER

Blooming habit: Continuous Spring and Fall.

Size of bloom: Small.

*Diameter.*—About 40 mm.

*Depth.*—About 20 mm.

Borne: Raceme.

Shape:

*When bloom first opens.*—High centered.

*When bloom matures.*—Becoming more-or-less flattened.

Petalage:

*Number of petals.*—About 30 to 40.

*Arrangement.*—Overlapping.

*Form.*—Generally fan shaped with serrated margin.

*Texture.*—Soft.

*Appearance.*—Shiny.

*Color.*—All petals: Top side and bottom side and for all seasons — Generally R.H.S. 43D with stripes of R.H.S. 43A, occasional petals variegated with white at their outer ends.

Flower stem:

*Length.*—Depending on season.
*Color.*—Dark Green.
*Character.*—Strong and upright.
Persistence: Petals hang on and dry.
Fragrance: Bloom is slightly fragrant.
Disease resistance: Generally resistant to fusarium oxysporum as observed at Aalsmeer, Holland.
Lasting quality:
*On plant.*—14 days.
*As cut flower.*—About 10 days.

REPRODUCTIVE ORGANS

Stamens: Of medium number.
*Anthers.*—Size: Medium. Color: Cream.
*Pollen.*—This flower has no pollen.

Pistils:
*Number.*—One. *Color.*—White/cream with pink at top end.

This plant is distinguished by its very unusual more-or-less pink and white variegation of various petals and by the unusual dark red longitudinal stripes appearing on many of the flower petals.

I claim:

1. The new and distinct carnation cultivar, substantially as herein shown and described, characterized by its continuous production of generally pink flowers somewhat variegated with white and occasional dark red longitudinal stripes.

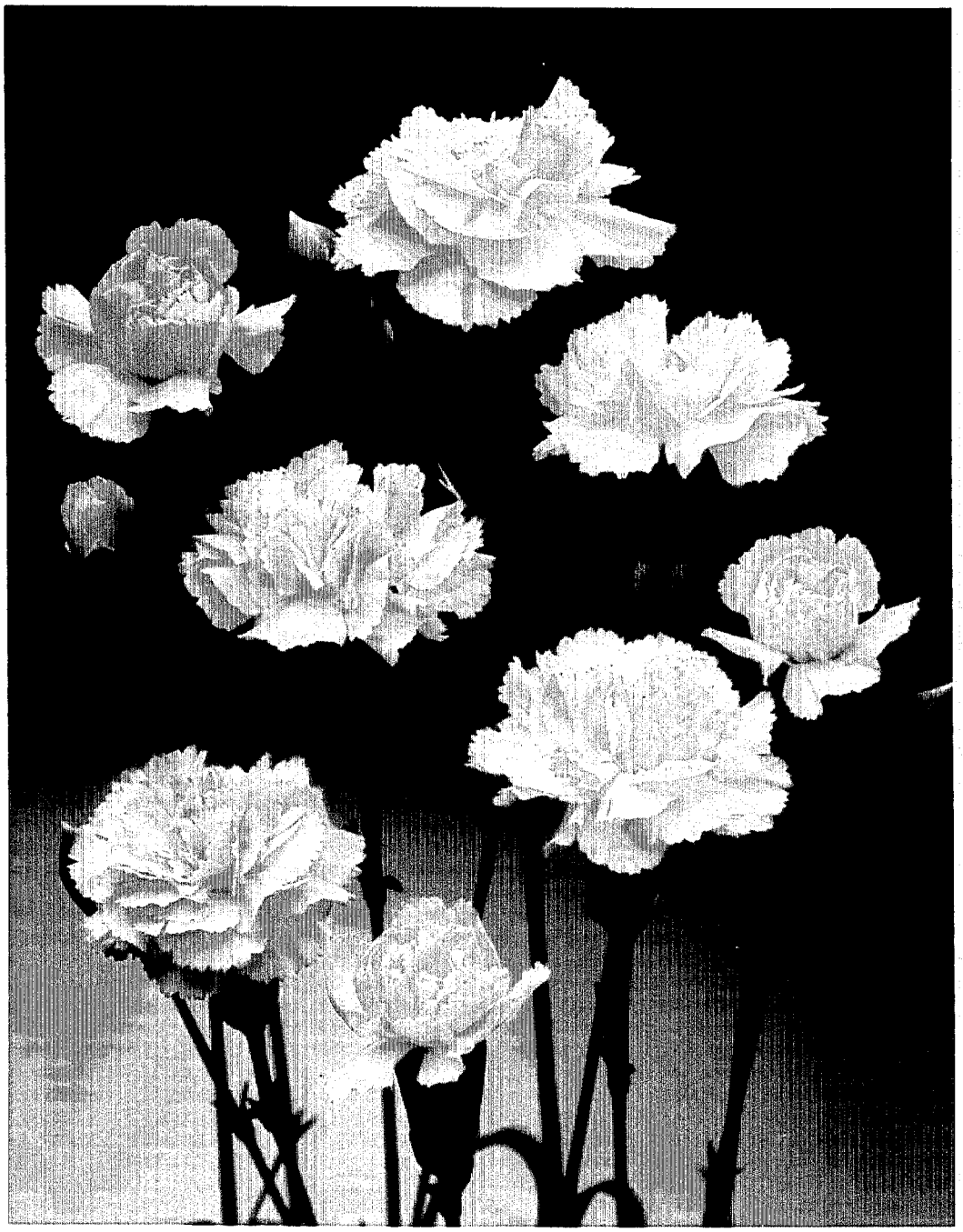

* * * * *